United States Patent [19]

Wilson

[11] Patent Number: 5,025,799
[45] Date of Patent: Jun. 25, 1991

[54] STEERABLE MEMORY ALLOY GUIDE WIRES

[76] Inventor: Bruce C. Wilson, 34 Twicwood La., Glens Falls, N.Y. 12801

[21] Appl. No.: 49,152

[22] Filed: May 13, 1987

[51] Int. Cl.$^5$ .............................................. A61B 5/00
[52] U.S. Cl. .................................... 128/772; 128/657; 604/95; 604/281
[58] Field of Search .................. 128/772, 656–658; 604/280–283

[56] References Cited

U.S. PATENT DOCUMENTS

| | | | |
|---|---|---|---|
| 3,868,956 | 3/1975 | Alfidi et al. | 128/345 |
| 3,890,977 | 6/1075 | Wilson | 604/281 |
| 4,215,703 | 8/1980 | Willson | 128/772 |
| 4,485,816 | 12/1984 | Krumme | 128/334 X |
| 4,568,338 | 2/1986 | Todd | 604/281 |
| 4,596,564 | 6/1986 | Spetzler et al. | 604/281 |
| 4,601,705 | 7/1986 | McCoy | 604/95 |
| 4,655,771 | 4/1987 | Wallsten | 604/281 X |
| 4,758,222 | 7/1988 | McCoy | 128/657 X |

FOREIGN PATENT DOCUMENTS 8603980 7/1986 PCT Int'l Appl. ................ 604/280

Primary Examiner—Max Hindenburg
Attorney, Agent, or Firm—Nixon & Vanderhye

[57] ABSTRACT

A medical guide wire or the like that is comprised in part or entirely of one or more heat activated memory alloys alone or in conjunction with one or more non-heat activated memory materials.

The tip or any portion of a guide wire comprised of memory alloy or components thereof can be aimed, deflected or steered on command by applying heat to the alloy. Combining heat activated memory alloys alone or with non-heat activated memory materials in opposite or antagonistic configurations or assemblies permits reversible shape change of the guide wire in any direction. The heat activated or shape memory alloys may be titanium-nickel alloys, titanium-nickel-cobalt alloys, other transition and precious metal alloys or thermoplastic heat settable material which exhibit shape memory characteristics. Heating of the guide wire is accomplished by induction heating, immersion heating, application of RF energy, or by body temperature.

17 Claims, 1 Drawing Sheet

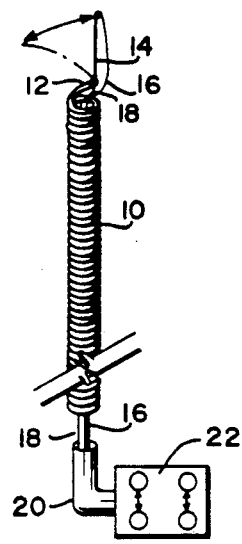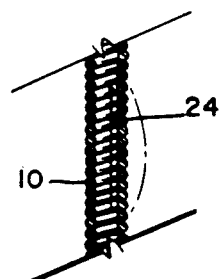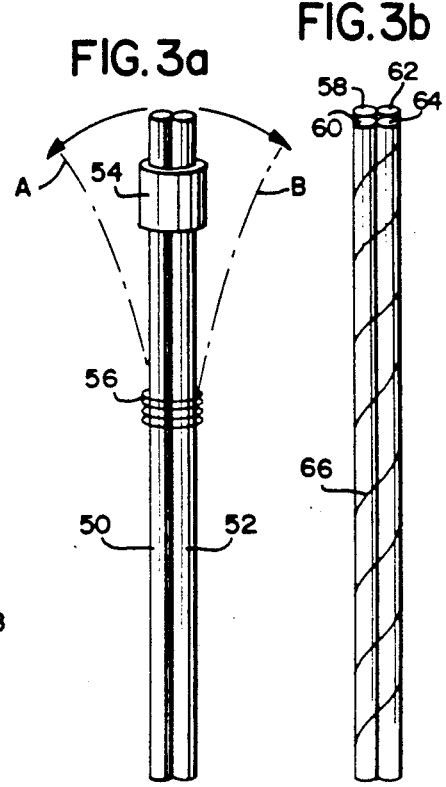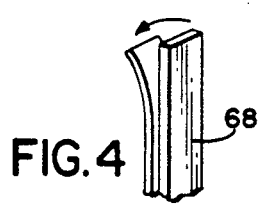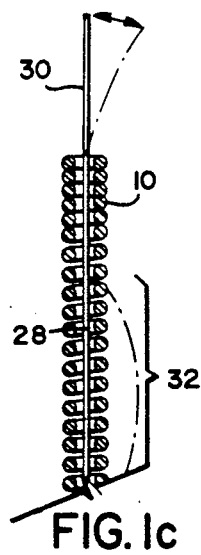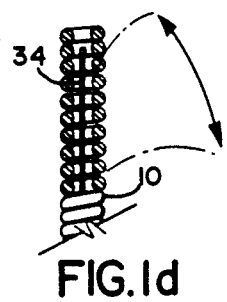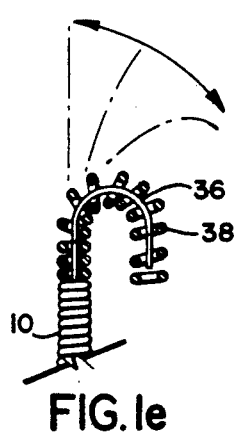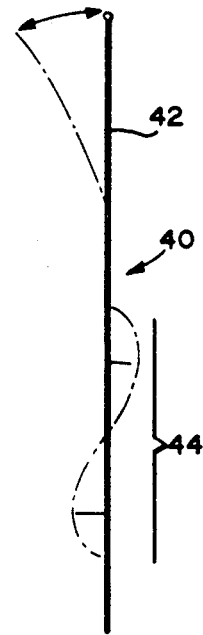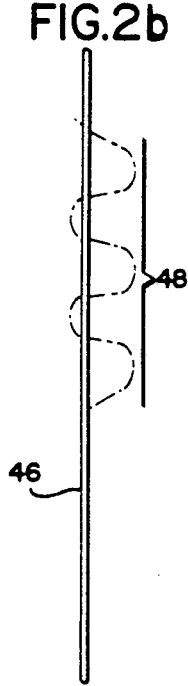

STEERABLE MEMORY ALLOY GUIDE WIRES

BACKGROUND AND SUMMARY OF THE INVENTION

This invention relates to guide wires which are steerable by reason of shape memory materials used in their construction.

A guide wire is a medical device that is typically formed of a long, flexible metal wire coiled or uncoiled, and having one or more components. They are generally used to gain access to a body structure or location by inserting it into the body and advancing it to the desired location. The guide wire can be used to probe, biopsy, penetrate, dilate or act as a vehicle for transporting an accompanying catheter to a given location.

It is, of course, desirable to provide a readily insertable guide wire that is also accurately steerable. Effective tip or body deflection of the wire, which provides the necessary steering capability, is important so that the guide wire can be quickly and accurately steered and guided through the desired path to the desired target structure or location within the body. In the past, guide wire designs have either lacked active steering capability, or they have incorporated mechanical steering designs which are large, awkward to use, and have limited steering characteristics. In this regard, typical guide wire constructions are shown in U.S. Pat. Nos. 4,619,274; 4,545,390; 4,538,622 and 3,528,406.

Quick, safe and effective steering of the guide wire is very important in many medical applications, especially in angioplasty procedures. For example, in percutaneous transluminal coronary angioplasty (PTCA) procedures, an inflatable balloon catheter is used to dilate narrow (stenotic) lesion sites within coronary arteries. A guide wire usually precedes an associated catheter by establishing passage through, and location of its distal tip at the site of the coronary artery narrowing, at which time the catheter is telescoped over the guide wire and advanced to the desired area. It will be appreciated that the anatomy of blood vessels in general, and especially so in coronary arteries, is very circuitous, or tortuous, with many side branches that complicate the successful passage of guide wires to their desired location. Thus, effective steering of the tip and/or body of the guide wire becomes very important for the quick, safe and accurate passage and placement of the guide wire preceding the transport and location of the PTCA catheter.

It is to be understood that the concept of a steerable guide wire is not limited to percutaneous transluminal coronary angioplasty (PTCA) procedures. Accurate steering capability is desirable in any guide wire used for any purpose such as, but not limited to, balloon and laser angioplasty, nephrostomy, angiography, electrode placement, etc.

SUMMARY OF THE INVENTION

The present invention provides a readily insertable and accurately steerable guide wire wherein the tip end, and/or selective body portions of the guide wire are comprised, at least in part, of a shape memory alloy. Shape memory alloys are those materials which exhibit mechanical memory triggered or activated by heat. Examples of such material are the titanium-nickel alloy disclosed in U.S. Pat. No. 3,174,851 and U.S. Pat. No. 3,672,879, as well as the titanium-nickel cobalt alloy disclosed in U.S. Pat. No. 3,558,369. The first mentioned alloy consists essentially of from 52 to 56% nickel by weight and correspondingly from about 48 to 44% titanium by weight. The alloy has the structure of a substantially TiNi phase from about 500° C. to about −75° C. This material is originally formed with restraint by annealing (typically at 950° to 1100° F.) into the shape desired when inserted into the body (such as a curve, angle or any other of an infinite variety of single or multiple configurations). The material is then deformed at a temperature (typically room temperature), below its transitional temperature (from about 32° to about 331° F. depending upon relative composition, but typically from 98° to 125° F.), into a shape facilitating easy insertion into the body, for example, in the form of a straight rod. The material is then incorporated into or attached to the guide wire structure.

When the guide wire is inserted into the body, the shape memory alloy can be activated on command by the application of heat to effect a deflection in the wire, enabling it to be steered in the desired path to its target location within the body.

Once heated to its transitional temperature, the shape memory alloy material will maintain its original shape even when cooled below its transitional temperature, if no external antagonistic force is applied.

The titanium-nickel cobalt alloy (Nitinol TM) disclosed in U.S. Pat. No. 3,558,369, has the formula $TiNi_x Co_{1-x}$ wherein Ti denotes titanium and constitutes approximately 50 atomic percent of the composition, and the term $Ni_x Co_{1-x}$ denotes nickel and cobalt respectively and make up the remaining approximately 50 atomic percent of the composition. X is a factor which varies from greater than 0 to less than 1 whereby the relative percentage of nickel and cobalt varies inversely from less than 100% to more than 0%. The transitional temperature of this alloy can be varied depending upon relative composition from −396° to +331° F. Otherwise, it is essentially the same as the above-mentioned titanium-nickel alloy.

It will be appreciated that shape memory materials other than titanium-nickel alloys such as Nitinol TM, may be effectively employed in the present invention. Titanium-copper alloys may also be used, and it is known that many other alloys of the transition and precious metals exhibit shape memory characteristics as well. Thermoplastic shape memory materials may also be used.

The present invention applies the shape memory alloy concept to provide accurate steering capability to guide wires in various forms. For example, it is well known to form a guide wire as a tightly, helically coiled spring. According to this invention, a shape memory alloy element is attached to the spring so as to extend beyond the distal tip of the spring. It is also contemplated to locate the shape memory alloy element within the lumen of the spring, in the distal tip portion, and/or at a location removed from the distal tip portion. In addition, while it is preferred to locate the element interiorly, it may be advantageous in some circumstances to locate the element on the exterior surface of the spring or use the element to construct all or part of the helical coil spring portion of the guide wire.

In another embodiment, the shape memory alloy element is in the form of a wire freely slidable within the helices of a tightly coiled spring. In this case, the wire may be previously selectively annealed at one or more spaced portions along its length. As the memory alloy is heated to its transitional temperature, the alloy curves to its annealed shape and thus bends the otherwise straightly aligned coils into the desired shape.

The guide wire may also consist only of a single strand of solid wire composed in part or entirely of shape memory alloy material, again with selectively applied shape memory characteristics. It will be understood that multiple curves generated at selected positions along the length of the wire may be used to both steer and/or anchor the guide wire.

In another embodiment, the guide wire comprises at least a pair of elongated shape memory wires, freely slidable with respect to each other but loosely held together by a helical wrap, sleeve or the like. In this embodiment, the shape memory members, or wires, are oriented so that one member changes shape in a direction opposite to the shape assumed by the other member. Thus, after applying a transitional temperature heat to one member to effect one shape, it is possible to later modify or reverse the first shape by activating another member of the guide wire assembly which is oriented to change shape in a direction diametrically opposed to the first member. In this way, the second member acts as an antagonist to the first member.

In each of the above embodiments, the memory alloy exerts greater force to retain its annealed shape when its transitional temperature is maintained. Thus, when the memory alloy is allowed to cool below its transitional temperature, the force of its memory in a given shape is reduced. By utilizing this phenomena in conjunction with memory alloy antagonists, accurate movement of the tips or selected body portions of alloy configured guide wires can be achieved. For example, if a tightly coiled but overall straight length of guide wire is fitted with one or more freely slidable memory alloy members, previously annealed to effect curved shapes upon heating, then as the transitional temperature is reached and maintained, the whole assembly will bend to conform to the annealed shape. However, as the heat source is withdrawn and the transitional temperature is not maintained, memory alloy force will be reduced so that, in properly dimensioned assemblies, the resilience of the coiled outer member will bend the inner alloy to a straight configuration. Conversely, if the tightly coiled helices are mechanically cold worked into curve or curves, and the memory alloy is annealed to effect a straight shape upon heating, then the guide wire will exhibit a curved shape below the transitional temperature state and, when brought to and maintained at the transitional temperature, the overall shape of the guide wire will become straight. When cooled below the transitional temperature, the resilient force of the coiled outer guide wire will be greater than the reduced memory force exerted by the alloy wire, and thus the guide wire will return to its original curved state.

Accordingly, heat activated memory alloy components can be combined with non-heat activated but structurally resilient materials to act antagonistically so that the tip or body of a guide wire can be steered to and/or fro on command in any of several multiple directions. It is thus possible to steer, aim or anchor the tip and/or body of the guide wire in one direction and then another, as well to rotate the entire guide wire assembly 360° about its axis so as to be reversibly omni-directional.

In addition to freely movable memory components of a guide wire, it is envisioned that in some embodiments, one or more memory components can be fastened or firmly attached to each other by welding, brazing, etc. so that upon heat activation of the memory components, certain desired bending or shaping would occur as a consequence of the members not being fully movable or slidable with respect to each other.

With respect to the manner in which the shape memory alloy materials are heated to the transitional temperature, various techniques may be employed. For example, induction heating, application of radio frequency (RF) energy, and immersion heating by water or other suitable solution, are effective. In addition, body heat may also be relied upon to effect shape change. In such case, it will be appreciated that the composition of the shape memory alloy material must be selected so that it has a transitional temperature at or just below body temperature.

Where induction heating is employed, the guide wire itself, any and all components thereof, as well as the electrical wires employed to pass current through the guide wire, may be insulated by a non-conductive sleeve, coating, etc. to prevent current leakage outside the device.

Accordingly, the present invention involves the construction of an improved guide wire or the like, utilizing in whole or in part, shape memory alloy materials which enable accurate deflection of the guide wire to steer it to a desired location, with or without further cooperation with a non-heat activated memory material.

Additional objects and advantages of the invention will become apparent from the detailed description and claims which follow.

BRIEF DESCRIPTION OF THE DRAWINGS

FIGS. 1a through 1e illustrate tightly coiled spring guide wires which incorporate shape memory alloy components in accordance with this invention;

FIGS. 2a and 2b illustrate a solid, single element guide wire composed entirely of a shape memory alloy in accordance with another embodiment of this invention;

FIGS. 3a and 3b illustrate guide wires comprising plural shape memory alloy components in accordance with still another embodiment of this invention; and FIG. 4 illustrates a rectangularly shaped memory alloy component for use with spring guide wires in accordance with the invention.

DETAILED DESCRIPTION OF THE INVENTION

Referring now to FIGS. 1a through 1e, tightly coiled spring guide wires 10 are disclosed which incorporate shape memory alloy components in different forms and in different locations in order to achieve an accurately steerable guide wire. In FIG. 1a, the coiled spring guide wire 10, which may be stainless steel or other suitable material, is fitted at its distal tip 12 with a substantially straight wire component 14 constructed of a shape memory alloy material that can be accurately steered or deflected in one plane as illustrated by the dotted line positions, when subjected to heat. Heating may be achieved by applying current to the component 14 by electrical wires 16, 18 which are enclosed in a suitable cable 20 and connected to a control unit 22. Heating of component 14 above its transitional temperature will result in deflection to a previously annealed shape, as indicated in phantom in FIG. 1.

The wires 16, 18 may be attached to the component 14 by any suitable means such as welding or brazing. It will be understood that the coiled spring itself could be utilized as the grounding wire, if it were constructed of a suitable electrically conductive material. As previously described, however, various other heating techniques may be employed which will enable component 14 to reach its transitional temperature, where it will assume its previously annealed shape to effect steering of the spring guide wire 10. Body temperature, immersion heating, and RF heating are considered exemplary but not limiting.

In FIG. 1b, the coiled spring guide wire 10 is fitted with a shape memory alloy component 24 at a point intermediate its ends, and preferably within the lumen of the spring, so that when heat is applied, the guide wire will bulge outwardly, as shown in phantom. It will be understood that the component 24 may also be attached to the exterior of the coiled spring guide wire. In either case, the component will be attached at one or both ends to individual coils of the spring, or at one or more points intermediate the ends of the component, but not along its entire length, since some relative motion must be permitted between the coils of the spring and the shape memory alloy component.

It will be appreciated that the coiled spring guide wires illustrated in FIGS. 1a, b and c may themselves be formed in part, or entirely, of a shape memory alloy, and annealed to assume one or more desired shapes when heated.

Turning now to FIG. 1c, a single, shape memory alloy wire 28 is illustrated running the full length of the coiled spring guide wire 10 and freely slidable with respect thereto. In this embodiment, selective sections of the wire, for example the tip 30, and one or more intermediate portions 32, may be previously annealed to variously curved shapes, whereas the remainder of the wire remains straight upon heating. Steering capability in this embodiment is enhanced since multiple curves in various directions are possible.

FIG. 1d illustrates a discrete memory component 34 fitted into the lumen of the coiled spring guide wire 10, and specifically, in the distal region thereof. The component 34 is mounted so that the alloy and the coils are slidable relative to one another, in order to accommodate the respective motion of each during a bending phase, which is again illustrated in phantom.

In FIG. 1e, a memory component 36 is fitted within the coils of the spring guide wire 10 in a manner similar to that shown in FIG. 1d. However, in this embodiment, the distal end portion 38 of the coiled spring itself may be cold-worked into a substantially J-shape or other curved configuration, with the shape memory alloy component 36 having been previously annealed in a straight line configuration. Thus, the force of the coils configured in the curved or substantially J-shape, will bend the memory alloy into a corresponding shape prior to the application of heat. However, when heat is applied to the memory alloy at the transitional temperature, and maintained, the shape memory alloy component 36 reverts to its straight annealed shape, overcoming the resilience of the coiled spring. When the heat is discontinued, and the memory alloy component 36 allowed to cool below its transitional temperature, the memory force is reduced whereby the resilience of the coiled spring again predominates, and the original J-shaped curve is once again achieved by reason of the coiled springs own mechanical memory. It will therefore be understood that the application of heat to the memory alloy and the subsequent discontinuance of heat and consequential cooling of the memory alloy below its transitional temperature is the operating principle by which guide wire steering capability may be effected in any desired direction and the reverse thereof.

FIG. 2a illustrates a single, solid guide wire 40 comprised in its entirety of a shape memory alloy material, wherein selected sections of the wire are previously annealed to various shapes while the remainder of the wire is annealed to a substantially straight line configuration. In this particular embodiment, the tip portion 42 is annealed to a curved shape, illustrated in phantom, and an intermediate section 44 is annealed to a sinusoidal shape to provide even greater steering capability.

FIG. 2b illustrates another single component, solid guide wire 46 wherein a forward or distal end portion 48 is annealed to a multiple curve, or deflection, configuration which enables the guide wire to be securely anchored at the desired location, so that it is not readily dislodged by pulling or pushing forces exerted, for example, by an associated catheter which is normally telescoped over the guide wire after the guide wire is steered to its final, desired position.

In FIG. 3a, still another arrangement is illustrated wherein two wire members 50, 52 of memory alloy material are held together by one or more plastic or metal sleeves 54 and/or ties 56. Members 54, 56 are free to slide longitudinally along the members 50, 52 which are also free to slide relative to each other to accommodate movement as required during the shaping or bending phase. In this example, the two wire members 50, 52 are substantially straight but may be annealed with curves which are 180° opposed as indicated by phantom positions A and B. It will thus be seen that the application of heat to member 50 will cause its deflection in one plane, to position A, with member 50 bringing the second member 52 along with it by reason of the presence of the one or more sleeves 54, or ties 56. Upon the application of heat to the second member 52, the curve in member 50 can be straightened out or if desired pulled 180° in the opposite direction to position B, as it conforms to its antagonist. In this fashion, a given bend or shape can be effected by heating one member and subsequently reversed, either to a straight configuration, or to a bend in the opposite direction by heating the second member. By combining two or more shape memory alloys, each having annealed shapes, the sequential and selective heating of one or more of the alloys, coupled with controlled rotation of the guide wire, can result in omni-directional and reversible steering as desired.

It will be understood that members 50, 52 may also be firmly attached to each other by welding, brazing, etc. (as shown in phantom in FIG. 3a) in order to obtain certain other desired bends or shapes which could not be achieved if the elements were freely slidable with respect to each other.

FIG. 3b operates in substantially the same manner as FIG. 3a, except that a group of four wire memory elements 58, 60, 62 and 64 are held together by a helical wrap 66 of Kevlar TM or other suitable material.

FIG. 4 illustrates a shape memory alloy component 68 useable in all of the above described embodiments. The component 68 is formed as one or more rectangular strips which may be preferable in certain applications. It will be understood, however, that this invention contemplates virtually any cross-sectional shape for the memory alloy including solid or hollow, round, oval, rectangular, square, triangular, etc.

It will be further understood that all of the above described guide wire constructions may be associated with control means which can effect rotation of the guide wires about a full 360° to achieve reversible and omni-directional steering capability.

Also, as explained previously, other transitional temperature activated mechanical memory materials can be utilized besides the above-mentioned titanium-nickel, titanium-nickel cobalt, and titanium-copper alloys. While the above-mentioned alloys are especially advantageous since the anneal and shape change cycle may be repeated indefinitely as long as the originally annealed temperature is not exceeded, thermoplastic or any other heat memory alloy materials may also be used.

Although preferred embodiments, uses and modifications of the inventions have been depicted and disclosed, such description is to be considered illustrative rather than limiting, particularly since those of ordinary skill in the art would understand that various modifications and changes may be made in the disclosed invention without departing from the spirit and scope of the claims which follow.

I claim:

1. A steerable guide wire adapted to be inserted within the body, and including shape memory alloy means for effecting accurate steering or aiming of said within the body, said guide wire comprising at least a pair of solid elongated shape memory wire members held in substantial coaxial engagement with each other but so as to allow relative sliding movement therebetween, and wherein one of said wire members is annealed to undergo a shape change in one direction upon application of heat, and another of said wire members is annealed to undergo a shape change in another direction upon application of heat, said guide wire being rotatable about 360° to thereby enable reversibly omni-directional steering of said guide wire.

2. A steerable guide wire as defined in claim 1 wherein said wire members are held together by at least one element slidable with respect to said wire members.

3. A steerable guide wire as defined in claim 1 wherein said wire members are held together by at least one tie member.

4. A steerable guide wire as defined in claim 1 wherein said wire members are held together by a strand helically wrapped about said wire members substantially along the entire length of said wire members.

5. A steerable guide wire as defined in claim 1 wherein said guide wire is shaped and sized for use as a vehicle to precede and position a catheter.

6. A steerable guide wire as defined in claim 1 wherein said guide wire is shaped and sized to precede and to serve as a vehicle for positioning an angioplasty catheter.

7. A steerable guide wire as defined in claim 1 wherein said guide wire is shaped and sized for use as a vehicle to precede and position an angiographic catheter.

8. A steerable guide wire as defined in claim 1 and further including means to effect heating of said shape memory wire members.

9. A steerable guide wire as defined in claim 8 wherein said heat effecting means comprises induction heating.

10. A steerable guide wire as defined in claim 9 wherein said guide wire is at least partially insulated with non-conductive material to prevent current leakage outside the guide wire.

11. A steerable guide wire as defined in claim 8 wherein said heat effecting means comprises body temperature.

12. A steerable guide wire is defined in claim 8 wherein said heat effecting means comprises immersion heating.

13. A steerable guide wire adapted to be inserted within the body, and including shape memory alloy means for effecting accurate steering or aiming of said within the body, wherein said guide wire comprises at least a pair of solid elongated shape memory wire members fixedly secured to each other to prevent relative movement therebetween, and wherein one of said wire members is annealed to undergo a shape change in one direction upon application of heat, and another of said wire members is annealed to undergo a shape change in another direction upon application of heat.

14. A steerable guide wire as defined in claim 1 wherein said shape memory alloy means is a titanium-nickel alloy.

15. A steerable guide wire as defined in claim 1 wherein said shape memory alloy means is comprised of a heat settable plastic material.

16. A steerable guide wire as defined in claim 1 wherein said shape memory alloy means is a titanium-nickel-cobalt alloy.

17. A steerable guide wire as defined in claim 1 wherein said shape memory alloy means is a titanium-copper alloy.

* * * * *